(12) United States Patent
Jennings et al.

(10) Patent No.: US 11,311,506 B2
(45) Date of Patent: Apr. 26, 2022

(54) CONTROLLING BIOFILMS WITH CYCLOPROPANATED FATTY ACIDS

(71) Applicant: THE UNIVERSITY OF MEMPHIS RESEARCH FOUNDATION, Memphis, TN (US)

(72) Inventors: Jessica Amber Jennings, Memphis, TN (US); Daniel Lee Baker, Memphis, TN (US); Rukhsana Awais, Memphis, TN (US); Zoe Harrison, Memphis, TN (US); Babatunde Raji, Memphis, TN (US)

(73) Assignee: THE UNIVERSITY OF MEMPHIS RESEARCH FOUNDATION, Memphis, TN (US)

( * ) Notice: Subject to any disclaimer, the term of this patent is extended or adjusted under 35 U.S.C. 154(b) by 25 days.

(21) Appl. No.: 16/670,802

(22) Filed: Oct. 31, 2019

(65) Prior Publication Data

US 2020/0138753 A1    May 7, 2020

Related U.S. Application Data

(60) Provisional application No. 62/754,302, filed on Nov. 1, 2018.

(51) Int. Cl.

| | | |
|---|---|---|
| *A61K 31/19* | (2006.01) | |
| *A61P 1/02* | (2006.01) | |
| *A01N 37/08* | (2006.01) | |
| *A61K 47/36* | (2006.01) | |
| *A61P 31/04* | (2006.01) | |

(52) U.S. Cl.
CPC ............... *A61K 31/19* (2013.01); *A01N 37/08* (2013.01); *A61K 47/36* (2013.01); *A61P 1/02* (2018.01); *A61P 31/04* (2018.01)

(58) Field of Classification Search
CPC .................................................... A61K 31/19
See application file for complete search history.

(56) References Cited

U.S. PATENT DOCUMENTS

| | | |
|---|---|---|
| 5,371,268 A | 12/1994 | Schuetz et al. |
| 6,455,031 B1 | 9/2002 | Davies et al. |
| 7,094,394 B2 | 8/2006 | Davies et al. |
| 2007/0207095 A1 | 9/2007 | Davies |
| 2012/0322769 A1 | 12/2012 | Yang et al. |
| 2014/0114055 A1 | 4/2014 | Lee et al. |
| 2016/0367722 A1 | 12/2016 | Bumgardner et al. |
| 2017/0118994 A1 | 5/2017 | Rautenbach et al. |

FOREIGN PATENT DOCUMENTS

| | | |
|---|---|---|
| FR | 2398714 A1 | 2/1979 |

OTHER PUBLICATIONS

Deng et al., "Diffusible signal factor (DSF) quorum sensing signal and structurally related molecules enhance the antimicrobial efficacy of antibiotics against some bacterial pathogens," BMC Microbiology, 2014; vol. 14, article No. 51, pp. 1-9.
Kolb et al., "Click Chemistry: Diverse Chemical Function from a Few Good Reactions," Angewandte Chemie International Edition, 2001; vol. 40, pp. 2004-2021.
Lebel et al., "Stereoselective Cyclopropanation Reactions," Chemical Reviews, 2003; vol. 103, No. 4, pp. 977-1050.
Wu et al., "The stabilization of electrospun chitosan nanofibers by reversible acylation," Cellulose, 2014; vol. 21, issue 4, pp. 2549-2556.
International Search Report and Written Opinion in corresponding PCT Patent Application No. PCT/US19/59210, dated Jan. 9, 2020 (51 pages).

*Primary Examiner* — Brian E McDowell
(74) *Attorney, Agent, or Firm* — Melissa Hunter-Ensor; Scott Goncher; Greenberg Traurig, LLP

(57) ABSTRACT

Compositions and methods for using cyclopropanated structural analogs of fatty acid biofilm dispersal agents are characterized by superior biofilm dispersion. When used in combination with antimicrobials, these analogs decrease the minimum inhibitory concentration of antimicrobial agents required for eradication of the biofilm and/or treatment of infection. Methods for using these analogs include direct application to a surface, blending with lipid based carriers, or covalent anchoring the molecule to a surface. Typically, the cyclopropanated structural analog has the structure according to formula (I):

(I)

[structure: cyclopropane ring with $R_1$ substituent and carboxylic acid group (C(=O)OH)]

wherein $R_1$ is a $C_1$-$C_{24}$ linear or branched alkyl group; or an acid halide or acid anhydride thereof.

7 Claims, 7 Drawing Sheets

CONTROLLING BIOFILMS WITH CYCLOPROPANATED FATTY ACIDS

CROSS REFERENCE TO RELATED APPLICATIONS

The present application claims the benefit of priority under 35 U.S.C. § 119 to U.S. App. No. 62/754,302, filed on Nov. 1, 2018, which is hereby incorporated by reference in its entirety.

STATEMENT OF FEDERALLY SPONSORED RESEARCH

This invention was made with government support under Grant No. R01 AR066050-01 awarded by National Institute of Health. The government has certain rights in this invention.

FIELD OF INVENTION

This invention relates to compositions of stabilized structural analogues of fatty acids that serve as diffusible signaling factors ("DSF"). The invention also relates to methods of use of these compositions to treat or prevent biofilm formation on a variety of surfaces. The compositions may also be used in methods of increasing the efficacy of antimicrobials.

BACKGROUND OF INVENTION

A biofilm is an aggregate of microbial cells that attaches to various surfaces, including tissue, complex wounds, implanted medical devices, industrial water supplies, marine plastic debris, and water columns. Almost 80% of human infections are due to the production of biofilm caused by pathogenic bacterial strains such as *Staphylococcus aureus, Staphylococcus epidermis, Pseudomonas aeruginosa*, and *Escherichia coli*. Additionally, these biofilms are problematic in a variety of other industries as well. For example, biofilms are able to form on plants and during industrial processes. Such formation results in increased spoilage of products and contaminated food products. Biofilms may form on marine equipment resulting in reduced hydrodynamic efficiency of ships and propellers, lead to pipeline blockage and sensor malfunction, and increase the weight of appliance deployed. Moreover, biofilms may act as a reservoir for potentially pathogenic bacteria in freshwater aquaculture.

Biofilms are formed when planktonic bacteria attach to a surface by the secretion of sugary complex termed extracellular polymeric substance (EPS) which encases the bacteria. The EPS is composed of polysaccharides, proteins, nucleic acids, and lipids which form strands that facilitate binding to surfaces. As the bacteria binds to surface, a complex matrix of bacteria is formed resulting in a cohesive polymer network of the EPS. The cohesive polymer network increases the mechanical stability of the biofilm and interconnects and immobilizes bacterial cells within it. Subgroups of bacterial cells within the biofilm, called persister cells, are dormant non-dividing cells which are resistant to antibiotics requiring cellular replication to elicit their effect.

The resistance of persister cells often increases the minimum inhibitory concentration of antibiotics up to 1000 times higher against bacteria present in biofilms as compared to planktonic bacteria. Currently, antimicrobial therapy is limited in cases of preformed bacterial cells which may cause pathogenic infections such as implant associated osteomyelitis, blood stream infections, pneumonia, or dental caries. Preventative anti-infective strategies in current practice include the local delivery of therapeutics, anti-biofilm coatings on surfaces and hygienic measures. However, additional strategies are required to improve efficacy of these treatments. Moreover, treatments of existing biofilms are particularly challenging. Once infection is present, the removal of implanted materials with aggressive debridement of affected tissue is often the only successful strategy for treating the infection.

Various fatty acids have been shown to disperse preformed biofilms or inhibit biofilm formation. An example is cis-decenoic acid (C2DA) which at a concentration of 500 μg/mL may inhibit bacterial growth while at 125 μg/mL C2DA is capable of inhibiting biofilm formation. Such short chain fatty acids are members of a family of diffusible signaling factors in bacteria which differ in overall chain length. It has been observed that these compounds revert persister cells to a metabolically active state which in combination with antimicrobials greatly decreases bacterial viability. Moreover, these compounds act to inhibit and disperse biofilms formed by multiple types of microorganisms.

Often these DSF compounds have one or more unsaturated bonds which are not particularly stable when exposed to light, elevated temperature, or radiation. These conditions, one or more of which may be used in the fabrication and/or sterilization of medical devices or therapeutics, can lead to isomerization of the alkene portion of the fatty acid DSF. Moreover, several DSFs are efficacious on biofilm formation due to the cis or trans like configuration of the fatty acid. For example, the cis-like (Z), configuration of C2DA may be converted to the trans-like (E) configuration under these conditions and effectiveness is decreased. Additionally, these unsaturated fatty acid DSFs are susceptible to oxidation resulting in saturated fatty acids which have less efficacy as well.

SUMMARY

In accordance with the foregoing objectives and others, the present invention provides compositions for removing and/or inhibiting biofilm production comprising compounds that have been found to not be plagued by those drawbacks described above. These compositions may be used to treat any manner of surfaces susceptible to biofilm production such as one or more surfaces of medical devices, marine equipment, industrial water systems food processing systems, reaction vessels and the like.

In one aspect, the invention provides a biofilm removing and/or inhibiting composition containing one or more compounds derived from a mono-unsaturated fatty acid, where the compound is cyclopropanated at the double bond of the fatty acid, and where the fatty acid is effective to remove or disrupt a bacterial biofilm or inhibit normal biofilm formation. In one embodiment, the fatty acid is a cis fatty acid. In another embodiment, the fatty acid has a terminal carboxylic acid. In another embodiment, the compound has the structure according to formula (I):

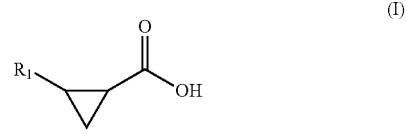

where R1 is a C1-C24 linear or branched alkyl group; or acid halides and acid anhydrides thereof. In another embodiment, the compound has the structure according to formula (Ia) and/or (Ib):

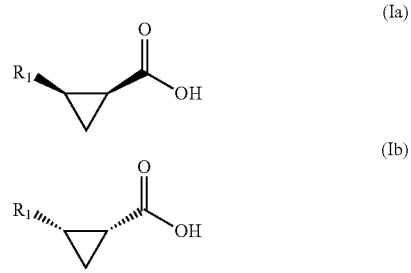

In another embodiment, the R1 is unsubstituted. In another embodiment, the R1 is a linear alkyl. In another embodiment, the compound has the structure:

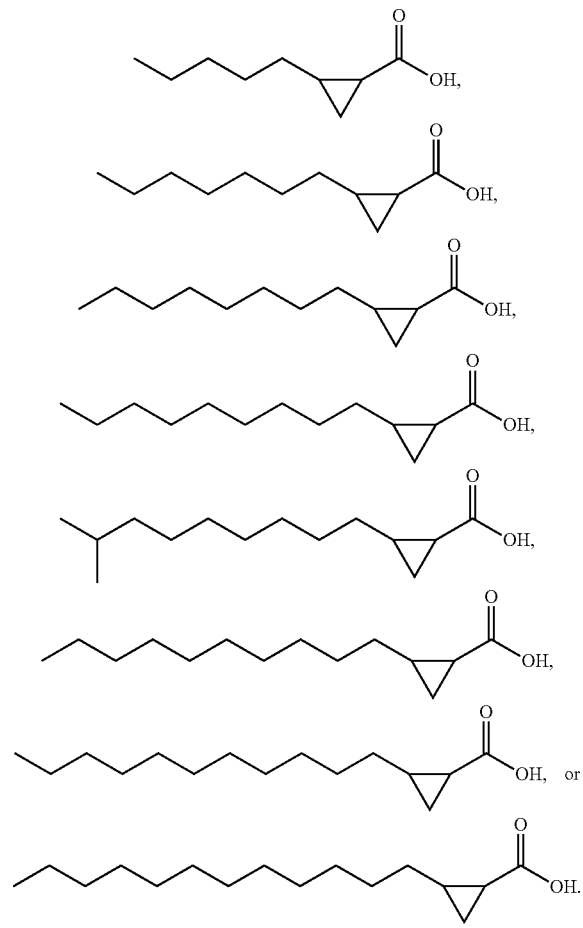

In another embodiment, the composition further contains an additive component selected from biocides, surfactants, antibiotics, antiseptics, detergents, chelating agents, virulence factor inhibitors, pharmaceutically acceptable carriers, excipients, or combinations thereof. In another embodiment, the composition contains an amount of the compound effective to remove or disrupt a bacterial biofilm or inhibit normal biofilm formation. In another embodiment, the composition is mouthwash or dentifrice. In another embodiment, the composition is a pharmaceutical composition further containing one or more pharmaceutically acceptable carriers or excipients. In another embodiment, the composition further contains an antibiotic (e.g., tobramycin, tetracycline, or levofloxacin).

In another aspect, the invention provides a method of preventing biofilm formation on a surface involving administering an effective amount of the composition according to any previous aspect to the surface. In one embodiment, the surface is on a medical device, an industrial water system, a marine vehicle, or a reaction vessel. In another embodiment, the surface is on the surface of a drainpipe, a contact lens, dentures, a glaze ceramic, porcelain, glass, metal, wood, chrome, plastic, vinyl, or Formica. In one embodiment, the surface is the surface of teeth (e.g., teeth with dental caries, etc.), skin (e.g., skin with acne, etc.), or bone.

In another aspect, the invention provides a method of inhibiting biofilm formation on a surface involving inserting one or more compounds derived from a mono-unsaturated fatty acid onto the surface, where the compound is cyclopropanated at the double bond of the fatty acid, and where the fatty acid is effective to remove or disrupt a bacterial biofilm or inhibit normal biofilm formation. In one embodiment, the surface is the surface of a biomaterial. In another embodiment, the surface contains chitosan and/or chitin. In another embodiment, the compound is adsorbed on the surface. In another embodiment, the compound is covalently attached to the surface. In another embodiment, the fatty acid is a cis fatty acid. In another embodiment, the fatty acid has a terminal carboxylic acid. In another embodiment, the compound has the structure according to formula (I):

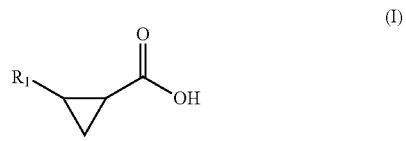

where R1 is a C1-C24 linear or branched alkyl group. In another embodiment, the compound has the structure according to formula (Ia) or (Ib):

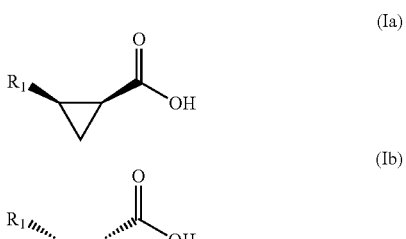

In another embodiment, the R1 is unsubstituted. In another embodiment, the R1 is a linear alkyl.

In another embodiment, the compound has the structure:

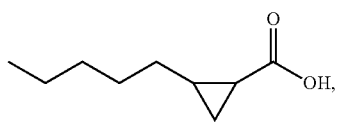

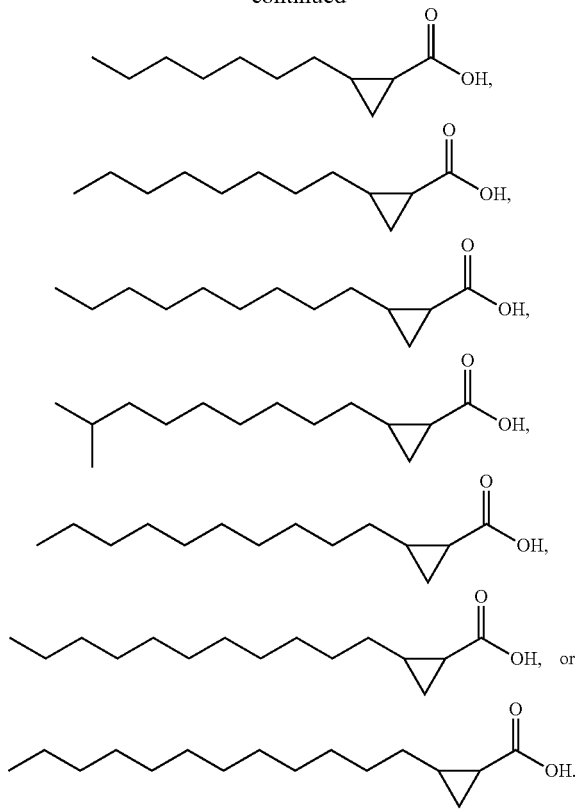

In another embodiment, the biofilm is produced by an organism selected from bacteria, algae, fungi, and protozoa. In another embodiment, the biofilm is produced by bacteria from the genus *Pseudomonas, Staphylococcus*, or *Escherichia*. In another embodiment, the biofilm is produced by bacteria from the species *Staphylococcus aureus, Staphylococcus epidermis, Pseudomonas aeruginosa*, and *Escherichia coli*.

In another aspect, the invention provides a method for the treatment or prevention of dental caries on one or more teeth or acne of skin containing administration of a composition according to any previous aspect to the one or more teeth or the skin.

In another aspect, the invention provides a biomedical device containing one or more compounds derived from a mono-unsubstituted fatty acid, where the compound is cyclopropanated at the double bond of the fatty acid, and where the fatty acid is effective to remove or disrupt a bacterial biofilm or inhibit normal biofilm formation. In one embodiment, the biomedical device is a local drug delivery apparatus, a wound dressing, or a bone regeneration graft. In one embodiment, the biomedical device contains chitosan loaded with the one or more compounds.

The compositions contain one or more compounds derived from an unsaturated fatty acid (e.g., a mono-unsaturated fatty acid, an acid halide of an unsaturated fatty acid, an acid anhydride of an unsaturated fatty acid, an acid halide of a mono-unsaturated fatty acid, an acid anhydride of a mono-unsaturated fatty acid etc.), wherein said compound is cyclopropanated at the double bond of said fatty acid, and wherein said fatty acid is effective to remove or disrupt a bacterial biofilm or inhibit normal biofilm formation. Many unsaturated fatty acids are known to be effective to remove, disrupt, or inhibit biofilm formation. Suitable unsaturated fatty acids are described in, for example, US Pub No 2007/0207095, U.S. Pat. Nos. 7,094,394, 6,455,031, and Deng Y. et al., *BMC Microbiology* 14 (2014): 51 (9 pages), each hereby incorporated by reference in their entirety and specifically in reference to fatty acid DSFs. The invention is partially premised on the discovery that cyclopropanated derivatives of these DSFs proffer increased benefits to compositions. The compositions may comprise a solvent and or carrier, and an additional component selected from biocides, surfactants, antibiotics, antiseptics, detergents, chelating agents, virulence factor inhibitors, pharmaceutically acceptable carriers, excipients, or combinations thereof.

In certain implementations, the compositions are pharmaceutical compositions comprising one or more cyclopropanated DSF compounds and one or more pharmaceutically acceptable carriers, excipients, and/or diluents. The pharmaceutical composition may further comprise an antibiotic (e.g., tobramycin, tetracycline, levofloxacin, etc.).

Methods of preventing, inhibiting, or removing biofilm formation on a surface are also provided, comprising administering an effective amount of the composition to the surface. Additionally, methods of inhibiting or preventing biofilm formation on a surface are provided, comprising inserting one or more compounds derived from an unsaturated fatty acid (e.g., an mono-unsaturated fatty acid, etc.) onto said surface. In certain embodiments, the surface is the surface of a medical device such as a local drug delivery device such as a polymer matrix or a coating to implants, tissues, and the like. In some embodiments, the cyclopropanated compounds may be used on membranes such as electrospun membranes. These membranes may be wound dressings or guided bone regeneration membranes.

DETAILED DESCRIPTION

Figure 1:
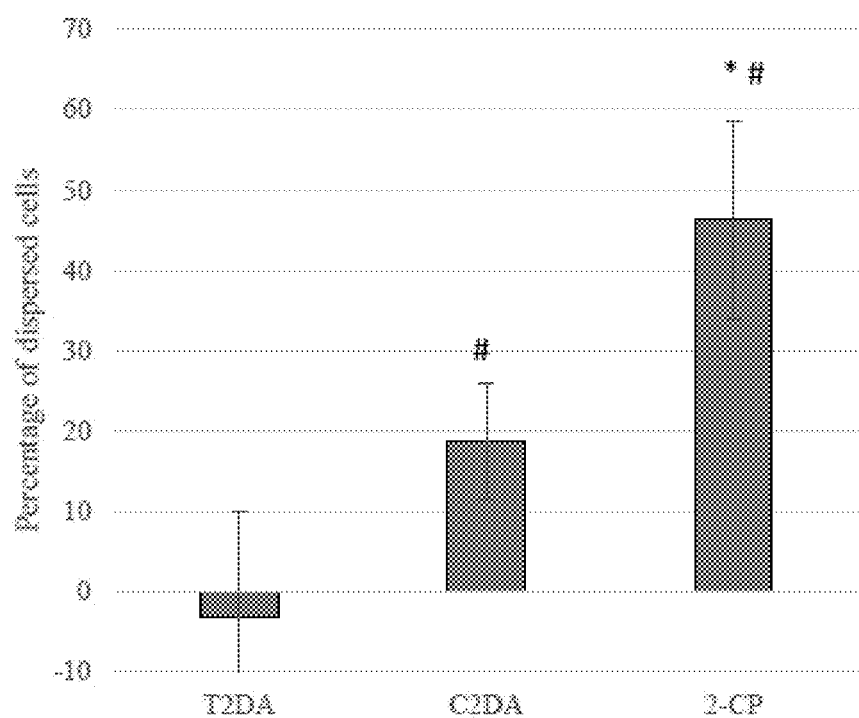
FIG. 1 illustrates the percentage of dispersed cells after 2 hours of exposure to T2DA, C2DA, or 2-CP. "#" represents statistically significant difference between group and T2DA, and "*" represents a statistically significant difference between group and C2DA as measured by one way ANOVA with Holm-Sidak post tests (p<0.05). Error bars are representative of standard deviation. N=3 for each group.
Figure 2:
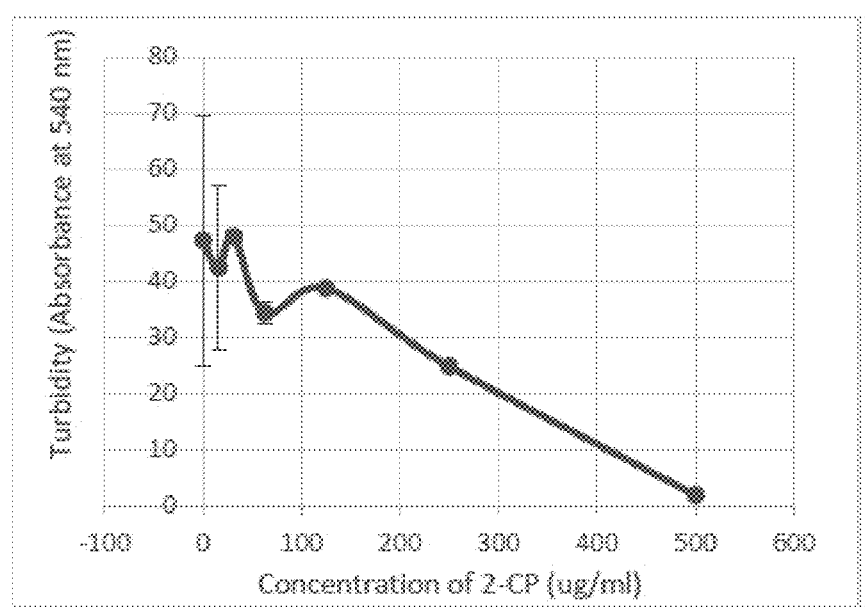
FIG. 2 illustrates the absorbance of wells with pegs following 24 hour incubation with 2-CP and 625 μg/mL tobramycin. Error bars are representative of standard deviation.

Detailed embodiments of the present invention are disclosed herein; however, it is to be understood that the disclosed embodiments are merely illustrative of the invention that may be embodied in various forms. In addition, each of the examples given in connection with the various embodiments of the invention is intended to be illustrative, and not restrictive.

All terms used herein are intended to have their ordinary meaning in the art unless otherwise provided. All concentrations are in terms of percentage by weight of the specified component relative to the entire weight of the topical composition, unless otherwise defined.

As used herein, "a" or "an" shall mean one or more. As used herein when used in conjunction with the word "comprising," the words "a" or "an" mean one or more than one. As used herein "another" means at least a second or more.

As used herein, all ranges of numeric values include the endpoints and all possible values disclosed between the disclosed values. The exact values of all half integral numeric values are also contemplated as specifically disclosed and as limits for all subsets of the disclosed range. For example, a range of from 0.1% to 3% specifically discloses a percentage of 0.1%, 1%, 1.5%, 2.0%, 2.5%, and 3%. Additionally, a range of 0.1 to 3% includes subsets of the original range including from 0.5% to 2.5%, from 1% to 3%, from 0.1% to 2.5%, etc. It will be understood that the sum of all weight % of individual components will not exceed 100%.

As used herein, the term "cyclopropanated" or "CP" refers to a compound wherein at least one carbon-carbon double bond in the molecule has been replaced with a cyclopropane group. The cyclopropyl group may be in cis or trans configuration but retains the cis or trans configuration of the double bond of the parent molecule (i.e., a cyclopropanated analog of a cis unsaturated compound will have cis configuration and a cyclopropanated analog of a trans unsaturated compound will have trans configuration). The cyclopropyl group may be substituted or unsubstituted.

As used herein, the term "alkyl," alone or in combination with other groups, refers to a branched or straight-chain monovalent saturated aliphatic hydrocarbon radical of 1-30 carbon atoms (e.g., 1-16 carbon atoms, 6-20 carbon atoms, 8-16 carbon atoms, or 4-18 carbon atoms, 4-12 carbon atoms, etc.). In some embodiments, the alkyl group may be substituted with 1, 2, 3, or 4 substituent groups as defined herein. Alkyl groups may have from 1-26 carbon atoms. In other embodiments, alkyl groups will have from 6-18 or from 1-8 or from 1-6 or from 1-4 or from 1-3 carbon atoms, including for example, embodiments having one, two, three, four, five, six, seven, eight, nine, or ten carbon atoms. Any alkyl group may be substituted or unsubstituted. Examples of alkyl groups include methyl, ethyl, propyl, butyl, pentyl, hexyl, heptyl, octyl, nonyl, decyl, undecyl, and dodecyl groups.

A "substituted" alkyl or cyclopropyl group may have as a substituent one or more hydrocarbon radicals, substituted hydrocarbon radicals, or may comprise one or more heteroatoms. Examples of substituted hydrocarbon radicals include, without limitation, heterocycles, such as heteroaryls. Unless otherwise specified, a hydrocarbon substituted with one or more heteroatoms will comprise from 1-20 heteroatoms. In other embodiments, a hydrocarbon substituted with one or more heteroatoms will comprise from 1-12 or from 1-8 or from 1-6 or from 1-4 or from 1-3 or from 1-2 heteroatoms. Examples of heteroatoms include, but are not limited to, oxygen, nitrogen, sulfur, phosphorous, halogen (e.g., F, Cl, Br, I, etc.), boron, silicon, etc. In some embodiments, heteroatoms will be selected from the group consisting of oxygen, nitrogen, sulfur, phosphorous, and halogen (e.g., F, Cl, Br, I, etc.). In some embodiments, a heteroatom or group may substitute a carbon. In some embodiments, a heteroatom or group may substitute a hydrogen. In some embodiments, a substituted hydrocarbon may comprise one or more heteroatoms in the backbone or chain of the molecule (e.g., interposed between two carbon atoms, as in "oxa"). In some embodiments, a substituted hydrocarbon may comprise one or more heteroatoms pendant from the backbone or chain of the molecule (e.g., covalently bound to a carbon atom in the chain or backbone, as in "oxo").

In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls. Moreover, where a moiety is substituted with an R substituent, the group may be referred to as "R-substituted." Where a moiety is R-substituted, the moiety is substituted with at least one R substituent and each R substituent is optionally different.

The term "substituent" refers to a group "substituted" on, e.g., an alkyl, at any atom of that group, replacing one or more hydrogen atoms therein. In some aspects, the substituent(s) on a group are independently any one single, or any combination of two or more of the permissible atoms or groups of atoms delineated for that substituent. In another aspect, a substituent may itself be substituted with any one of the above substituents. Further, as used herein, the phrase "optionally substituted" means unsubstituted (e.g., substituted with an H) or substituted. It is understood that substitution at a given atom is limited by valency.

Unless otherwise noted, all groups described herein may optionally contain one or more common substituents, to the extent permitted by valency. Common substituents include halo (e.g., F, Cl, etc.), $C_{1-12}$ straight chain or branched chain alkyl, $C_{2-12}$ alkenyl, $C_{2-12}$ alkynyl, $C_{3-12}$ cycloalkyl, $C_{6-12}$ aryl, $C_{3-12}$ heteroaryl, $C_{3-12}$ heterocyclyl, $C_{1-12}$ alkylsulfonyl, nitro, cyano, —COOR, —C(O)NRR', —OR, —SR, —NRR', and oxo, such as mono- or di- or tri-substitutions with moieties such as halogen, fluoroalkyl, perfluoroalkyl, perfluoroalkoxy, trifluoromethoxy, chlorine, bromine, fluorine, methyl, methoxy, pyridyl, furyl, triazyl, piperazinyl, pyrazoyl, imidazoyl, and the like, each optionally containing one or more heteroatoms such as halo, N, O, S, and P. R and R' are independently hydrogen, $C_{1-12}$ alkyl, $C_{1-12}$ haloalkyl, $C_{2-12}$ alkenyl, $C_{2-12}$ alkynyl, $C_{3-12}$ cycloalkyl, $C_{4-24}$ cycloalkylalkyl, $C_{6-12}$ aryl, $C_{7-24}$ aralkyl, $C_{3-12}$ heterocyclyl, $C_{3-24}$ heterocyclylalkyl, $C_{3-12}$ heteroaryl, or $C_{4-24}$ heteroarylalkyl. Further, as used herein, the phrase "optionally substituted" means unsubstituted (e.g., substituted with H) or substituted. The term "substituted" means that a hydrogen atom is removed and replaced by a substituent (e.g., a common substituent). It is understood by one of ordinary skill in the chemistry art that substitution at a given atom is limited by valency. The use of a substituent (radical) prefix names such as alkyl without the modifier "optionally substituted" or "substituted" is understood to mean that the particular substituent is unsubstituted. However, the use of "haloalkyl" without the modifier "optionally substituted" or "substituted" is still understood to mean an alkyl group, in which at least one hydrogen atom is replaced by halo.

In some embodiments, the alkyl group may be substituted with one or more click chemistry functionalities. Such functionalities are described in H. Kolb et. al., *Chem. Int. Ed.* 40 (2001): 2004-2021, hereby incorporated by reference in its entirety. Such substitution may allow for bioconjugation to surfaces. For example, the alkyl may be substituted with azide, alkynyl, nitrone, and strained alkene functional groups.

Compounds provided herein can have one or more asymmetric carbon atoms and can exist in the form of optically pure enantiomers, mixtures of enantiomers such as racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with a chiral adsorbent or eluant). That is, certain of the disclosed compounds may exist in various stereoisomeric forms. Stereoisomers are compounds that differ only in their spatial arrangement. Enantiomers are pairs of stereoisomers whose mirror images are not superimposable, most commonly because they contain an asymmetrically substituted carbon atom that acts as a chiral center. "Enantiomer" means one of a pair of molecules that are mirror images of each other and are not superimposable. Diastereomers are stereoisomers that are not related as mirror images, most commonly because they contain two or more asymmetrically substituted carbon atoms and represent the configuration of substituents around one or more chiral carbon atoms. Enantiomers of a compound can be prepared, for example, by separating an enantiomer from a racemate using one or more well-known techniques and methods, such as chiral chromatography and separation methods based thereon. The appropriate technique and/or method for separating an enantiomer of a compound described herein from a racemic mixture can be readily determined by those of skill in the art. "Racemate" or "racemic mixture" means a mixture containing two enantiomers, wherein such mixtures exhibit no optical activity; i.e., they do not rotate the plane of polarized light. "Geometric isomer" means isomers that differ in the orientation of substituent atoms (e.g., to a carbon-carbon double bond, to a cycloalkyl ring, to a bridged bicyclic system, etc.). Atoms (other than H) on each side of a carbon-carbon double bond may be in an E (substituents are on opposite sides of the carbon-carbon double bond) or Z (substituents are oriented on the same side) configuration. "R," "S," "S*," "R*," "E," "Z," "cis," and "trans," indicate configurations relative to the core molecule. Certain of the disclosed compounds may exist in atropisomeric forms. Atropisomers are stereoisomers resulting from hindered rotation about single bonds where the steric strain barrier to rotation is high enough to allow for the isolation of the conformers. The compounds disclosed herein may be prepared as individual isomers by either isomer-specific synthesis or resolved from an isomeric mixture. Conventional resolution techniques include forming the salt of a free base of each isomer of an isomeric pair using an optically active acid (followed by fractional crystallization and regeneration of the free base), forming the salt of the acid form of each isomer of an isomeric pair using an optically active amine (followed by fractional crystallization and regeneration of the free acid), forming an ester or amide of each of the isomers of an isomeric pair using an optically pure acid, amine or alcohol (followed by chromatographic separation and removal of the chiral auxiliary), or resolving an isomeric mixture of either a starting material or a final product using various well known chromatographic methods.

When the stereochemistry of a disclosed compound is named or depicted by structure, the named or depicted stereoisomer is at least 60%, 70%, 80%, 90%, 99%, or 99.9%) by weight relative to the other stereoisomers. When a single enantiomer is named or depicted by structure, the depicted or named enantiomer is at least 60%, 70%, 80%, 90%, 99%, or 99.9% by weight optically pure. When a single diastereomer is named or depicted by structure, the depicted or named diastereomer is at least 60%, 70%, 80%, 90%, 99%, or 99.9% by weight pure. Percent optical purity is the ratio of the weight of the enantiomer or over the weight of the enantiomer plus the weight of its optical isomer. Diastereomeric purity by weight is the ratio of the weight of one diastereomer or over the weight of all the diastereomers. When the stereochemistry of a disclosed compound is named or depicted by structure, the named or depicted stereoisomer is at least 60%, 70%, 80%, 90%, 99%, or 99.9% by mole fraction pure relative to the other stereoisomers. When a single enantiomer is named or depicted by structure, the depicted or named enantiomer is at least 60%, 70%, 80%, 90%, 99%, or 99.9% by mole fraction pure. When a single diastereomer is named or depicted by structure, the depicted or named diastereomer is at least 60%, 70%, 80%, 90%, 99%, or 99.9% by mole fraction pure. Percent purity by mole fraction is the ratio of the moles of the enantiomer or over the moles of the enantiomer plus the moles of its optical isomer. Similarly, percent purity by moles fraction is the ratio of the moles of the diastereomer or over the moles of the diastereomer plus the moles of its isomer. When a disclosed compound is named or depicted by structure without indicating the stereochemistry, and the compound has at least one chiral center, it is to be understood that the name or structure encompasses either enantiomer of the compound free from the corresponding optical isomer, a racemic mixture of the compound or mixtures enriched in one enantiomer relative to its corresponding optical isomer. When a disclosed compound is named or depicted by structure without indicating the stereochemistry and has two or more chiral centers, it is to be understood that the name or structure encompasses a diastereomer free of other diastereomers, a number of diastereomers free from other diastereomeric pairs, mixtures of diastereomers, mixtures of diastereomeric pairs, mixtures of diastereomers in which one diastereomer is enriched relative to the other diastereomer(s) or mixtures of diastereomers in which one or more diastereomer is enriched relative to the other diastereomers. The disclosure embraces all of these forms.

It will be understood that the description of compounds herein is limited by principles of chemical bonding known to those skilled in the art. Accordingly, where a group may be substituted by one or more of a number of substituents, such substitutions are selected so as to comply with principles of chemical bonding with regard to valencies, etc., and to give compounds which are not inherently unstable. For example, any carbon atom will be bonded to two, three, or four other atoms, consistent with the four valence electrons of carbon.

The term "effective amount" or "therapeutically effective amount" of an agent, as used herein, is that amount sufficient to effect beneficial or desired results, such as clinical results, and, as such, an "effective amount" depends upon the context in which it is being applied. For example, in the context of administering an agent that is an antibiotic agent, an effective amount of an agent is, for example, an amount sufficient to achieve alleviation or amelioration or prevention or prophylaxis of one or more symptoms or conditions; diminishment of extent of disease, disorder, or condition; stabilized (i.e., not worsening) state of disease, disorder, or condition; preventing spread of disease, disorder, or condition; delay or slowing the progress of the disease, disorder, or condition; amelioration or palliation of the disease, disorder, or condition (e.g., tooth decay, acne, etc.); and remission (whether partial or total), whether detectable or undetectable, as compared to the response obtained without administration of the agent.

An effective amount of the active compounds for the cleaning of a surface may be the amount of compound necessary to remove some bacteria for the surface as determined by a reduction in numbers of bacteria within the biofilm when compared to an otherwise identical biofilm not exposed to the compound. An effective amount for cleaning may remove at least 10% of the bacteria from the surface (e.g., at least 20%, at least 30%, etc.).

An effective amount of the active compounds for preventing biofilm formation may be the amount required to prevent biofilm formation between normal cleaning times, most preferably preventing any biofilm build-up as determined by a statistically significant increase in the number of cells within a biofilm or upon a clean surface. Prevention of normal biofilm formation may be determined by the ability to disperse a biofilm using surfactants and/or detergents and/or other chemical treatments which will result in the removal of bacterial cells from a biofilm. To distinguish between normal biofilm formation and treatment with a prevention-effective amount of the active compounds described herein, the treated biofilm may release 10% or more (e.g., 20% or more, 30% or more, etc.) when compared to a similar biofilm that is not treated when both biofilms are exposed to surfactants and/or detergents and/or other chemical treatments which will result in the removal of bacterial cells from a biofilm. For example, the composition may comprise from 0.1% to 95% (e.g., from 1% to 20%, from 20% to 40%, from 40% to 60%, from 60% to 80%, or from 80% to 95%, etc.) of the cyclopropanated DSF by weight of the composition and one or more carriers, solvent, diluents, or excipients. In some embodiments, the invention may relate to biofilm removing or inhibiting composition comprising one or more compounds described herein and an additive component selected from biocides, surfactants, antibiotics, antiseptics, detergents, chelating agents, virulence factor inhibitors, pharmaceutically acceptable carriers, excipients, or combinations thereof.

The term "pharmaceutical composition," as used herein, represents a composition containing a compound described herein formulated with a pharmaceutically acceptable excipient. In some embodiments, the pharmaceutical composition is manufactured or sold with the approval of a governmental regulatory agency as part of a therapeutic regimen for the treatment of disease in a mammal. Pharmaceutical compositions can be formulated, for example, for oral administration in unit dosage form (e.g., a tablet, capsule, caplet, gel cap, or syrup); for topical administration (e.g., as a cream, gel, lotion, or ointment); for intravenous administration (e.g., as a sterile solution free of particulate emboli and in a solvent system suitable for intravenous use); or in any other formulation described herein (see below).

Useful pharmaceutical carriers for the preparation of the compositions hereof, can be solids, liquids, or gases. Thus, the compositions can take the form of tablets, pills, capsules, suppositories, powders, enterically coated or other protected formulations (e.g., binding on ion-exchange resins or packaging in lipid-protein vesicles), sustained release formulations, solutions, suspensions, elixirs, and aerosols. The carrier can be selected from the various oils including those of petroleum, animal, vegetable or synthetic origin, e.g., peanut oil, soybean oil, mineral oil, and sesame oil. Water, saline, aqueous dextrose, and glycols are preferred liquid carriers, particularly (when isotonic with the blood) for injectable solutions. For example, formulations for intravenous administration comprise sterile aqueous solutions of the active ingredient(s) which are prepared by dissolving solid active ingredient(s) in water to produce an aqueous solution, and rendering the solution sterile. Suitable pharmaceutical excipients include starch, cellulose, chitosan, talc, glucose, lactose, gelatin, malt, rice, flour, chalk, silica, magnesium stearate, sodium stearate, glycerol monostearate, sodium chloride, dried skim milk, glycerol, propylene glycol, water, and ethanol. The compositions may be subjected to conventional pharmaceutical additives such as preservatives, stabilizing agents, wetting or emulsifying agents, salts for adjusting osmotic pressure, and buffers. Suitable pharmaceutical carriers and their formulation are described in Remington's Pharmaceutical Sciences by E. W. Martin. Such compositions will, in any event, contain an effective amount of the active compound together with a suitable carrier so as to prepare the proper dosage form for administration to the recipient.

As used herein, the term "pharmaceutically acceptable salt" refers to salts of any of the compounds described herein that within the scope of sound medical judgment, are suitable for use in contact with the tissues of humans and animals without undue toxicity, irritation, allergic response and are commensurate with a reasonable benefit/risk ratio. Pharmaceutically acceptable salts are well known in the art. For example, pharmaceutically acceptable salts are described in: Berge et al., *J. Pharmaceutical Sciences* 66:1-19, 1977 and in *Pharmaceutical Salts: Properties, Selection, and Use*, (Eds. P. H. Stahl and C. G. Wermuth), Wiley-VCH, 2008. Salts may be prepared from pharmaceutically acceptable non-toxic acids and bases including inorganic and organic acids and bases. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, dichloroacetate, digluconate, dodecylsulfate, ethanesulfonate, formate, fumarate, glucoheptonate, glutamate, glycerophosphate, hemisulfate, heptonate, hexanoate, hippurate, hydrobromide, hydrochloride, hydroiodide, 2-hydroxy-ethanesulfonate, isethionate, lactobionate, lactate, laurate, lauryl sulfate, malate, maleate, malonate, mandelate, methanesulfonate, mucate, 2-naphthalenesulfonate, nicotinate, nitrate, oleate, oxalate, palmitate, pamoate, pantothenate, pectinate, persulfate, 3-phenylpropionate, phosphate, picrate, pivalate, propionate, stearate, succinate, sulfate, tartrate, thiocyanate, toluenesulfonate, undecanoate, and valerate salts. Representative basic salts include alkali or alkaline earth metal salts include sodium, lithium, potassium, calcium, and magnesium, aluminum salts, as well as nontoxic ammonium, quaternary ammonium, and amine cations, including, but not limited to ammonium, tetramethylammonium, tetraethylammonium, methylamine, dimethylamine, trimethylamine, triethylamine, caffeine, and ethylamine.

As used herein, the term "subject" refers to any organism to which a composition in accordance with the disclosure may be administered, e.g., for experimental, diagnostic, prophylactic, and/or therapeutic purposes. In most embodiments, the subject is a human. Other subjects may include mammals such as mice, rats, rabbits, cats, dogs, non-human primates. The subject may be domesticated animals (e.g., cows, calves, sheep, goat, lambs, horses, poultry, foals, pigs, piglets, etc.), or animals in the family Muridae (e.g., rats, mice, etc.), or animals in the family Felidae. A subject may seek or be in need of treatment, require treatment, be receiving treatment, may be receiving treatment in the future, or a human or animal that is under care by a trained professional for a particular disease or condition (e.g., dental caries, etc.).

The term "unit dosage form" refers to a physically discrete unit suitable as a unitary dosage for human subjects and other mammals, each unit containing a predetermined quantity of active material calculated to produce the desired therapeutic effect, in association with any suitable pharmaceutical excipient or excipients. Exemplary, non-limiting unit dosage forms include a tablet (e.g., a chewable tablet), caplet, capsule (e.g., a hard capsule or a soft capsule), lozenge, film, strip, gel cap, and syrup (also see below).

The compounds are cyclopropanated derivatives of naturally occurring fatty acids including acid halides and acid anhydrides thereof. In some embodiments, the fatty acid is a cis fatty acid. In some embodiments, the fatty acid is a terminal carboxylic acid. For example, the compound may have the structure according to formula (I):

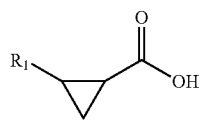
(I)

wherein $R_1$ is a $C_1$-$C_{24}$ linear or branched alkyl group;
and acid halides, acid anhydrides, pharmaceutically acceptable salts, and pharmaceutically acceptable prodrugs thereof. In certain implementations, the compound has the structure according to formula (Ia) and/or (Ib):

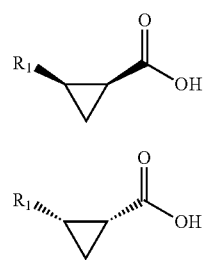

or acid halides or acid anhydrides thereof. In some embodiments, $R_1$ is unsubstituted. In other embodiments, $R_1$ is substituted (e.g., substituted with one or more click chemistry functional groups such as azide, alkynyl, and nitrone functional groups). In some embodiments, $R_1$ is linear alkyl. In some embodiments, $R_1$ is selected from pentyl, hexyl, heptyl, octyl, nonyl, decyl, undecyl, dodecyl, 4-methylpentyl, 5-methylhexyl, 6-methylheptyl, 7-methyloctyl, 8-methylnonyl, 9-methyldecyl, 10-methylundecyl, or 11-methyldodecyl. In certain implementations, the compound is cis-2-heptylcyclopropanyl-1-carboxylic acid or an acid halide (e.g., acid chloride, acid fluoride, etc.) or an acid anhydride thereof.

In certain embodiments, the compound has the structure:

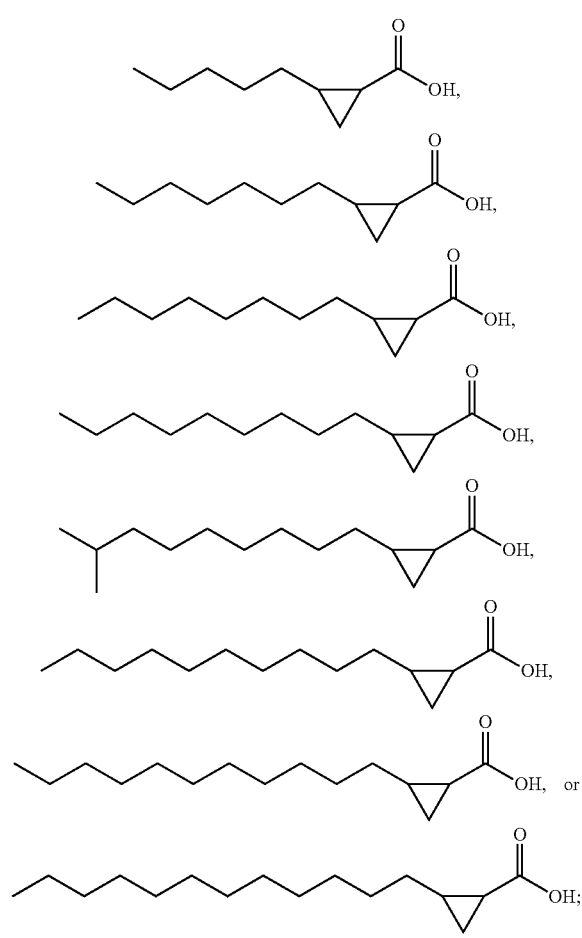

or an acid halide or acid anhydride thereof.

In some embodiments, the biofilm removing or inhibiting composition is a pharmaceutical composition. Pharmaceutical compositions are provided having one or more cyclopropanated DSFs (e.g., compounds having the structure of formula (I), etc.), and one or more pharmaceutically acceptable carriers or excipients. In most embodiments, the pharmaceutical composition may be used for the treatment or prophylaxis of bacterial infection. In some embodiments, the pharmaceutical composition may be used for the treatment or prophylaxis of biofilm formation and/or bacterial infection.

For use in the methods described herein, the compounds can be formulated as pharmaceutical compositions. The formulation selected can vary depending on the subject to be treated, the mode of administration, and the type of treatment desired (e.g., prevention, prophylaxis, or therapy). A summary of formulation techniques is found in *Remington: The Science and Practice of Pharmacy*, 21$^{st}$ Edition, Lippincott Williams & Wilkins, (2005); and *Encyclopedia of*

*Pharmaceutical Technology*, eds. J. Swarbrick and J. C. Boylan, 1988-1999, Marcel Dekker, New York, each of which is incorporated herein by reference. Exemplary routes of administration and formulations are described as follows.

In the practice of the disclosed methods, the compounds (or pharmaceutically acceptable salts thereof) or compositions can be administered by any of the usual and acceptable routes and methods known in the art. The compounds or compositions can thus be administered, for example, by the enteral or gastrointestinal route (e.g., orally or rectally), topically (e.g., to the skin or an accessible mucous membrane (e.g., an intraoral (e.g., sublingual or buccal), intranasal, intrarectal, or genitourinary surface)), parenterally (e.g., by intramuscular, intravenous, subcutaneous, intraarticular, intravesicular, intrathecal, epidural, ocular, or aural application or injection), transdermally, or by inhalation (e.g., by aerosol).

The compositions can be in the form of a solid, liquid, or gas, as determined to be appropriate by those of skill in the art. Thus, as general examples, the pharmaceutical compositions may be in the form of tablets, capsules, syrups, pills, enterically coated or other protected formulations, sustained release formulations, elixirs, powders, granulates, suspensions, emulsions, solutions, gels (e.g., hydrogels), pastes, ointments, creams, plasters, transdermal patches, drenches, suppositories, enemas, injectables, implants, sprays, or aerosols.

The compositions, in general, include an effective amount of the compound described herein (i.e., the cyclopropanated DSF, etc.) and one or more pharmaceutically acceptable carriers or excipients, as is well known in the art. The compositions can thus include one or more diluents, buffers, preservatives, salts, carbohydrates, amino acids, carrier proteins, fatty acids, lipids, etc. The compounds described herein may be present in amounts totaling, for example, 0.1-95% by weight of the total weight of the composition (e.g., 0.1-1% by weight of the composition, 1-10% by weight of the composition, 10-20% by weight of the composition, 20-30% by weight of the composition, 30-40% by weight of the composition, etc.). In some embodiments, the pharmaceutical composition may have a concentration of the cyclopropanated DSF (e.g., cyclopropanated fatty acids having the structure of formula (I) of between 0.1 and 5000 µg/mL (e.g., 1 and 2000 µg/mL, 1 and 1000 µg/mL, 50 and 800 µg/mL, 200 and 700 µg/mL, etc.).

For injection, formulations can be prepared in conventional forms as liquid solutions or suspensions, or as solid forms suitable for solution or suspension in liquid prior to injection, or as emulsions. Suitable excipients for these formulations include, for example, water, saline, dextrose, and glycerol. Such compositions can also contain nontoxic auxiliary substances, such as wetting or emulsifying agents, and pH buffering agents, such as sodium acetate, sorbitan monolaurate, and so forth.

Formulations for oral use include tablets containing a compound in a mixture with one or more non-toxic pharmaceutically acceptable excipients. These excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Other pharmaceutically acceptable excipients can be colorants, flavoring agents, plasticizers, humectants, and buffering agents.

Formulations for oral use may also be provided as chewable tablets, or as hard gelatin capsules wherein the active ingredient is mixed with an inert solid diluent (e.g., potato starch, lactose, microcrystalline cellulose, calcium carbonate, calcium phosphate or kaolin), or as soft gelatin capsules wherein the active ingredient is mixed with water or an oil medium, for example, peanut oil, liquid paraffin, or olive oil. Powders, granulates, and pellets may be prepared using the ingredients mentioned above under tablets and capsules in a conventional manner using, e.g., a mixer, a fluid bed apparatus or a spray drying equipment.

Dissolution or diffusion controlled release can be achieved by appropriate coating of a tablet, capsule, pellet, or granulate formulation of compounds, or by incorporating the compound into an appropriate matrix. A controlled release coating may include one or more of the coating substances mentioned above and/or, e.g., shellac, beeswax, glycowax, castor wax, carnauba wax, stearyl alcohol, glyceryl monostearate, glyceryl distearate, glycerol palmitostearate, ethylcellulose, acrylic resins, dl-polylactic acid, cellulose, chitosan, acetate butyrate, polyvinyl chloride, polyvinyl acetate, vinyl pyrrolidone, polyethylene, polymethacrylate, methylmethacrylate, 2-hydroxymethacrylate, methacrylate hydrogels, 1,3 butylene glycol, ethylene glycol methacrylate, and/or polyethylene glycols. In a controlled release matrix formulation, the matrix material may also include, e.g., hydrated methylcellulose, carnauba wax and stearyl alcohol, carbopol 934, silicone, glyceryl tristearate, methyl acrylate-methyl methacrylate, polyvinyl chloride, polyethylene, and/or halogenated fluorocarbon.

The liquid forms in which the compounds and compositions can be incorporated for administration orally include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

The dose of a compound depends on a number of factors, such as the manner of administration, the age and the body weight of the subject, and the condition of the subject to be treated, and ultimately will be decided by the attending physician or veterinarian. Such an amount of the compound, as determined by the attending physician or veterinarian, is referred to herein, and in the claims, as a "therapeutically effective amount." For example, the dose of a compound disclosed herein is typically in the range of about 1 to about 1000 mg per day. Preferably, the therapeutically effective amount is in an amount of from about 1 mg to about 500 mg per day.

Administration of each drug, as described herein, can, independently, be one to four times daily for one day to one year, and may even be for the life of the subject. Chronic, long-term administration may be indicated.

The methods described herein include the treatment or prevention of dental caries on one or more teeth in need thereof. Such methods include administering a composition comprising one or more cyclopropanated DSFs (e.g., compounds having the structure of formula (I), etc.) to the teeth.

Such administration may be achieved, for example through use of a pharmaceutical formulation in the form of mouthwash or dentifrice.

The methods also include the treatment or prevention of acne to a subject in need thereof. Such methods include administering of a composition comprising one or more cyclopropanated DSFs (e.g., compounds having the structure of formula (I), etc.) to skin in need of such treatment. Such compositions may be formulated as topical compositions. In some embodiments, the topical composition is in the form of a cream, ointment, gel, or tonic.

In some embodiments, the compositions may be administered to a wound to treat or prevent infection and/or biofilm formation. Methods of treating or preventing infection are provided comprising administering a composition comprising one or more cyclopropanated DSFs (e.g., compounds having the structure of formula (I), etc.) to an area in need thereof (e.g., skin, a wound, the mouth, a tooth, etc.). Such compositions may be formulated as topical compositions. In some embodiments, the topical composition is in the form of a cream, ointment, gel, or tonic.

The compounds and compositions can be packaged in a kit, optionally with one or more other pharmaceutical agents (see below). Non-limiting examples of the kits include those that contain, e.g., two or more pills, a pill and a powder, a suppository and a liquid in a vial, or two topical creams. The kits can include optional components that aid in the administration of the unit dose to subjects, such as vials for reconstituting powder forms, syringes for injection, customized IV delivery systems, or inhalers. Additionally, the unit dose kits can contain instructions for preparation and administration of the compositions. The kits can be manufactured as a single use unit dose for one subject, multiple uses for a particular subject (at a constant dose or in which the individual compounds may vary in potency as therapy progresses); or the kits can contain multiple doses suitable for administration to multiple subjects ("bulk packaging"). The kit components can be assembled in cartons, blister packs, bottles, and tubes.

The compounds and pharmaceutical compositions can be formulated and employed in combination therapies, that is, the compounds and pharmaceutical compositions can be formulated with or administered concurrently with, prior to, or subsequent to, one or more other desired therapeutics or medical procedures. The particular, combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder, or they may achieve different effects (e.g., control of any adverse effects). In some embodiments, the combination therapy may comprise administration of one or more cyclopropanated fatty acid compounds and one or more antibiotic. The cyclopropanated fatty acid may provide an increased effect on the antibiotic (e.g., decreasing the minimum inhibitory concentration, etc.) properties of the antibiotic as compared to the antibiotic alone and/or the cyclopropanated fatty acid alone. In some embodiments, the antibiotic may be selected from erythromycin and ester prodrugs/derivatives thereof, such as erythromycin stearate and erythromycin estolate; clarithromycin, roxythromycin, azithromycin, aureomycin, oleandomycin, sulfisoxazole, spiramycin, troleandomycin, josamycin, cytovaricin, linezolid, eperezolid, clindamycin, lincomycin, quinupristin, dalfopristin, streptomycin, amikacin, gentamicin, kanamycin, neomycin, tobramycin, netilmicin, paromomycin, tetracycline, chlortetracycline, doxycycline, minocycline, declomycin, methacycline, spectinomycin, and oxytetracycline, and combinations thereof. In certain embodiments, the composition has weight ratio of cyclopropanated fatty acid derivative to antibiotic of 10:1 to 1:10 (e.g., 5:1 to 1:5, 8:1 to 1:8, 2:1 to 1:2, 10:1 to 1:1, 5:1 to 1:1, 2:1 to 1:1, 1:1 to 1:10, 1:1 to 1:5, 1:1 to 1:2, etc.).

The biofilm is an aggregate of microbial cells that attaches to various surfaces which may be produced by an organism selected from bacteria, algae, fungi, and protozoa. In some embodiments, the biofilm is produced by bacteria from the genus *Pseudomonas, Staphylococcus,* or *Escherichia*. In certain embodiments, the biofilm is produced by bacteria from the species *Staphylococcus aureus, Staphylococcus epidermis, Pseudomonas aeruginosa,* and *Escherichia coli*.

The present invention relates to compounds which induce a physiological dispersion response in bacterial cells in a biofilm. Surfaces coated with these compounds are also encompassed by the invention.

The compounds may be used to treat surfaces to prevent the formation of a biofilm. In some embodiments, the compounds may be used to treat surface with biofilms formed thereon. Any surface where biofilms form may be treated with the compounds of the invention. For example, the surface may be on a medical device, industrial water system, marine vehicle, or reaction vessel. In some embodiments, the surface may be on a medical device including one or more surfaces of a catheter, respirator, ventilator, stent, artificial valve, joint, pin, and other temporary or permanent medical devices. In some embodiments, the surface includes one or more surfaces of drains, tubs, kitchen appliances, countertops, shower curtains, grout, toilets, industrial food and beverage production facilities. In some embodiments, the compound is impregnated in a surface in order to inhibit formation of a biofilm on the surface. Alternatively, the compounds may spread on a surface, for example by administering the compound in a copolymer, gel, or polymeric film forming composition over a surface.

In some embodiments, the compounds may be used in connection with local drug delivery applications and medical devices therefore. In some embodiments, the compounds may be incorporated onto the surface of a local drug delivery apparatus for implantation into a treatment site of a living organism and at least one active agent in releasable therapeutic dosages affixed to the surface of the apparatus. In certain embodiments, the compounds may be loaded onto the surface of the apparatus to prevent biofilm formation. In some embodiments, the compounds may be used with nanoparticles, nanocapsules, hydrogels, nanotubes, liposomes, nanogels, dendrimers, stents for local drug delivery and the like. In some embodiments, the cyclopropanated compounds may be incorporated into a polymer matrix or applied as a coating to implants, tissues, or other materials.

The cyclopropanated compounds may also be used in biomedical membranes such as guided bone regeneration membranes or wound dressings to prevent biofilm formation from the use of such devices. The use of these biomedical membranes is often plagued by biofilm formation. Implantation of the compounds described herein provides the ability to reduce or prevent the formation of biofilms around such devices. For example, wound dressing are generally used to cover wounds in an effort to assist in the wound healing process and guided bone regeneration membranes direct the healing and formation of tissues by preventing the overgrowth of fast healing epithelial tissues into areas of more slowly healing tissues. The membrane may be made of a wide variety of materials including chitosan, chitin, alginate, cellulose acetate, cellulose, hyaluronic acid, collagen, silk, gelatin, polyurethane, poly(L-lactide), poly(c-caprolactone), polyacrylonitrile, poly(acrylamide)/poly(vinyl sulfonic acid sodium salt), and poly (vinyl alcohol), or blends thereof. In some embodiments, the membrane may be electrospun. In certain implementations, the membrane comprises electronspun chitosan and one or more the of the compounds to prevent biofilm formation.

The cyclopropanated compounds may be loaded onto biomaterial such as chitin or chitosan. In some embodiments, the compounds may be loaded onto a biomaterial to prevent formation of a biofilm. In some embodiments, the compounds may be loaded onto a biomaterial for release from the membrane following insertion into a media comprising a biofilm forming microbe (e.g., bacteria, etc.). In some embodiments, the compounds are loaded non-covalently onto chitosan. Exemplary non-covalent loading of cis-2-heptylcyclopropanyl-1-carboxylic acid may be depicted by the following structure:

weight ratio of cyclopropanated DSF to biomaterial may be 10:1 to 1:10 (e.g., 5:1 to 1:5, 8:1 to 1:8, 2:1 to 1:2, 10:1 to 1:1, 5:1 to 1:1, 2:1 to 1:1, 1:1 to 1:10, 1:1 to 1:5, 1:1 to 1:2, etc.).

The device may comprise a surface coated with one or more compounds derived from a cis fatty acid that is a diffusible signaling factor, wherein said compound is cyclopropanated with respect to the double bond of said cis fatty acid. The device may be a medical device, an industrial water system, a marine vehicle, or a reaction vessel. In some embodiments, one or more surfaces of the device is impregnated with the compound. In some embodiments, the surface of the device is covalently loaded with the compounds of the invention. In other embodiments, the surface of the device is non-covalently loaded with the compounds of the invention. In some embodiments, the surface of the device is both covalently and non-covalently loaded with the compounds of the invention.

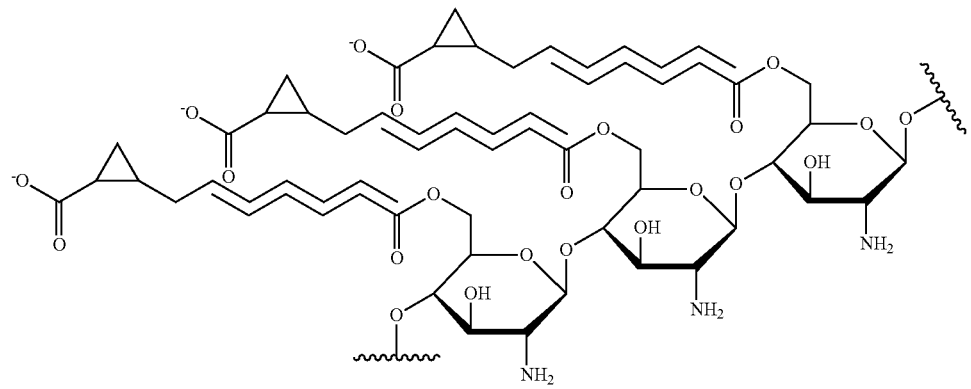

Additionally, the compounds may be loaded covalently. For example, the compounds may be loaded through reaction of the carboxylic acid moiety to produce loaded chitosan having the structure:

EXAMPLES

The following examples illustrate specific aspects of the instant description. The examples should not be construed as

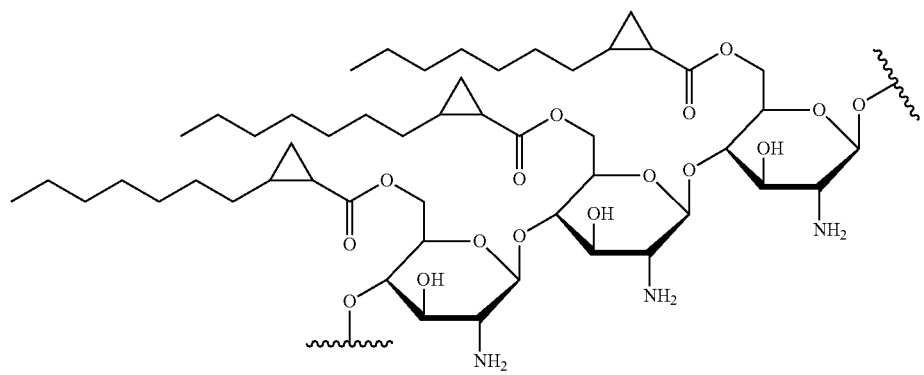

The effect may be modulated by alteration of the weight ratio of the cyclopropanated DSF (e.g., cyclopropanated fatty acid having the structure of formula (I), etc.) to biomaterial (e.g., chitosan, chitin, etc.). For example, the limiting, as the example merely provides specific understanding and practice of the embodiments and its various aspects. Additional compounds not specifically exemplified may be synthesized using conventional methods in combination with the methods described herein. For example, cyclopropanation techniques may be found in H. Lebel, et. al., Chem Rev. 103 (2003): 977-1050, hereby incorporated by reference in its entirety.

Example 1: Synthesis of Cyclopropanated Fatty Acid DSFs

Synthesis of gram quantities of cis-2-decenoic acid (C2DA), trans-2-decenoic acid (T2DA), and cis-2-heptyl-cyclopropanyl-1-carboxylic acid (2-CP) were performed using a combination of Lindlar reduction, Jones oxidation, and cyclopropanation to make all three targets. One synthetic route to the production of the cyclopropanated compounds is:

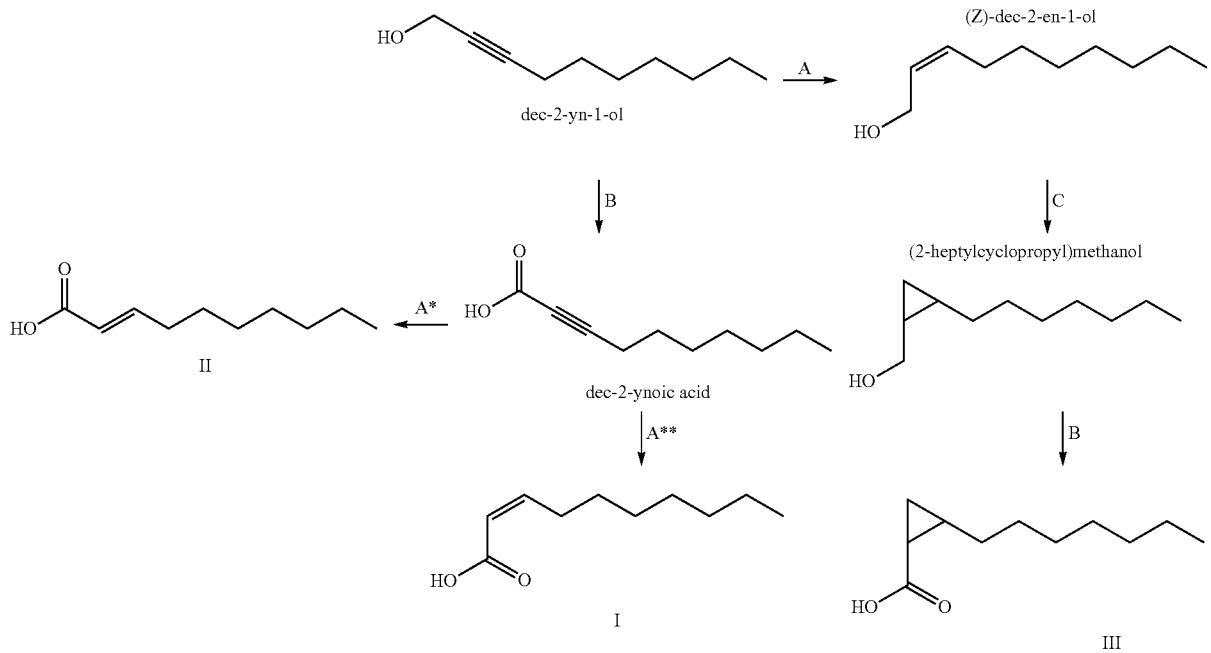

In the schema, step (A) was performed with Lindlar catalyst, ethyl acetate, hydrogen gas, step (B) was performed with Jones reagent and acetone at 0° C. to room temperature left overnight, and step (C) was performed with diethyl zinc, diiodomethane, tetrahydrofuran (THF), hexanes at −40° C., overnight. Step (A*) occurs in ethanol and step (A**) occurs in THF.

Example 2: Biofilm Dispersion Measurements (*Staphylococcus aureus*)

Biofilm was formed using *Staphylococcus aureus* in a 96-well plate format. Each well of the plate was seeded with 150 µL of bacterial culture and incubated for 24 hours to allow for biofilm growth. The medium in each well was changed every 24 hours for 5 days and every 12 hours for two additional days. On day 7, 135 µL of Tryptic Soy Broth (TSB) and 15 µL of C2DA, T2DA, or 2-CP were added to yield final concentrations of each test compound ranging from 0 to 1000 µg/mL. The plate was then incubated for one hour and the turbidity of each solution was determined at 540 nm. Bacterial growths were then aspirated from all wells and the plates were washed several times with water.

The relative percentage of attached cells as compared to non-treated controls was assessed using a Luciferase assay for ATP production. FIG. 1 shows the results measured percentage of dispersed cells following addition of 500 µg/mL T2DA, C2DA, or 2-CP. As can be seen, the cyclopropanated 2-CP has increased ability to disperse biofilm as compared to its unsaturated fatty acid analog, C2DA.

Example 3: Biofilm Eradication with Antibiotics

Overnight cultures of *Staphylococcus aureus* were prepared by inoculating 2 mL of TSB followed by incubation overnight at 37° C. The following day, 1 mL of this stock was diluted in 10 mL of TSB. A total of 150 µL of the diluted stock was seeded into each well of a 96-well MBEC™ Biofilm Inoculator plate, followed by incubation overnight to allow biofilm growth. All media and planktonic bacteria were then aspirated from each well thus allowing the biofilm to remain both on the bottom of each well and on the pegs on the top of the plate. Stocks of tobramycin or tetracycline (625 µg/mL antibiotic in each), as well as varying concentrations of C2DA or 2-CP (ranging from 0-500 µg/mL of each fatty acid) were added to the wells. The plates were incubated for 24 hours at 37° C.

Following incubation, the pegs were removed and added to new plates containing 150 µL of sterile TSB in each well. Plates and pegs were then sonicated for 5 minutes to remove any viable bacteria attached to the pegs, followed by incubation for 24 hours. Turbidity was determined via absorbance at 540 nm to access bacterial growth in the presence of fixed concentration of antibiotics and varying concentrations of C2DA and 2-CP. In this assay, the live bacteria that remained attached to the pegs grew overnight and increased turbidity. The turbidity was significantly lower (i.e., fewer bacteria survived) in the presence of increasing concentration of 2-CP with fixed concentrations of tobramycin (FIG.

Figure 3:
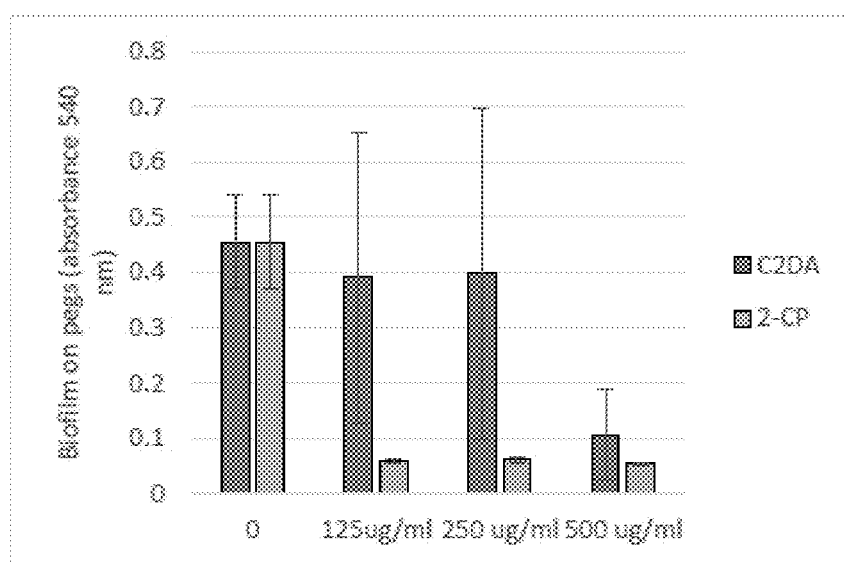
FIG. 3 illustrates the absorbance of wells at 24 hour incubation with C2DA and 2-CP at concentrations ranging from 0-500 μg/mL in combination with 625 μg/mL tetracycline. Error bars are representative of standard deviation.

2). When used in combination with tetracycline at 625 µg/mL, 2-CP eradicated the biofilm at lower concentrations than C2DA (FIG. 3).

Example 4: Cytocompatibility

Figure 4:
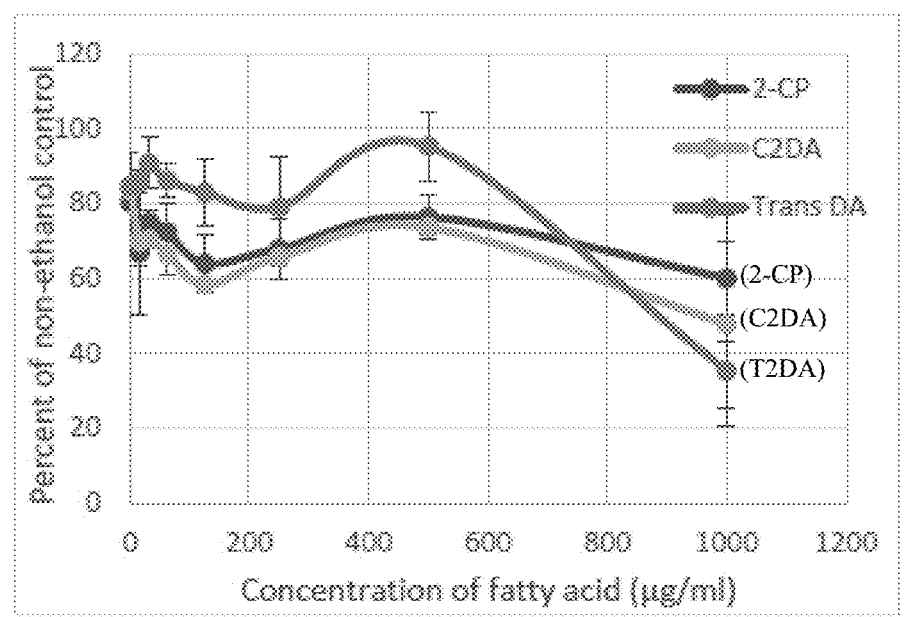
FIG. 4 illustrates the cytocompatibility assay results showing the percentage of viable cells compared to no-additive controls 24 hour after addition of fatty acids. Error bars are representative of standard deviation.

Mouse fibroblast cells (NIH3T3) were seeded (1×10$^4$ cells/cm$^2$) in 24-well plates in Dulbecco's Modified Eagle's Medium (DMEM) supplemented with 10% fetal bovine serum and 100 µg/mL Normocin for 24 hours at 37° C. and 5% $CO_2$. Concentrations of C2DA, T2DA, and 2-CP ranging from 0 to 1000 µg/mL were added to various wells. The plate was incubated for 24 hours and cell viability was measured using CellTiter Glow. FIG. 4 illustrates the measured chemiluminescence from the assay as a percentage of a phosphate-buffered saline (PBS) control which did not comprise the test compounds. As can be seen, 2-CP has a cytocompatibility equal to C2DA (i.e., it is no more toxic than C2DA and only exhibits significant cytotoxicity toward mammalian cells at 1000 µg/mL).

Example 5: Incorporation into Biomaterials

Chitosan membranes (polymers of N-acetyl glucosamine where less than 50% of possible C2 amino groups are acetylated) were fabricated by electrospinning as described in Wu, C. X., et al., Cellulose 21 (2014): 2549-2556 and Wu, C., et al., *Chitosan Nanofiber Compositions and Methods of Use*, U.P. Application, Ed. 2014, each hereby incorporated by reference in their entirety. Membranes were treated post-spinning using hexanoic anhydride (HA). This fatty acid reacts with primary C5 hydroxyl groups of chitosan and protects the polymeric chain from excessive swelling thereby increasing the hydrophobic nature and mechanical properties of the membrane. This reaction was carried out by immersing membranes in a solution of pyridine and HA 1:1 (v/v) for 1 hour. The membranes were then washed in MilliQ water 3 times to remove unreacted pyridine and HA. The washed membranes were frozen and lyophilized until further use.

Chitosan membranes (5 mm in diameter, 3.1-5 mg) were loaded noncovalently with either 1000 µg, 500 µs, 250 µg or 0 µg of 2-CP. Noncovalent loading of chitosan with 2-CP is thought to have the repeating structure:

Membranes of these four different loading groups were incubated in PBS at 37° C. for 14 days with complete PBS refreshment daily. Membranes were collected at day 0 (immediately after loading, no elution), day 7 and day 14. Membranes were placed in a culture of 10$^4$ colony forming units (CFU) of *Staphylococcus aureus*. After incubation for 24 hours, membranes were removed and washed in sterile PBS two times to remove non-adherent bacteria. Washed membranes were sonicated for 5 minutes to remove attached bacteria. Relative numbers of attached bacteria were determined using PrestoBlue cell viability reagent. In addition, absorbance of wells from which membranes were removed was determined after twice washing with PBS to determine the biofilm inhibition due to 2-CP released from membranes.

Figure 5:
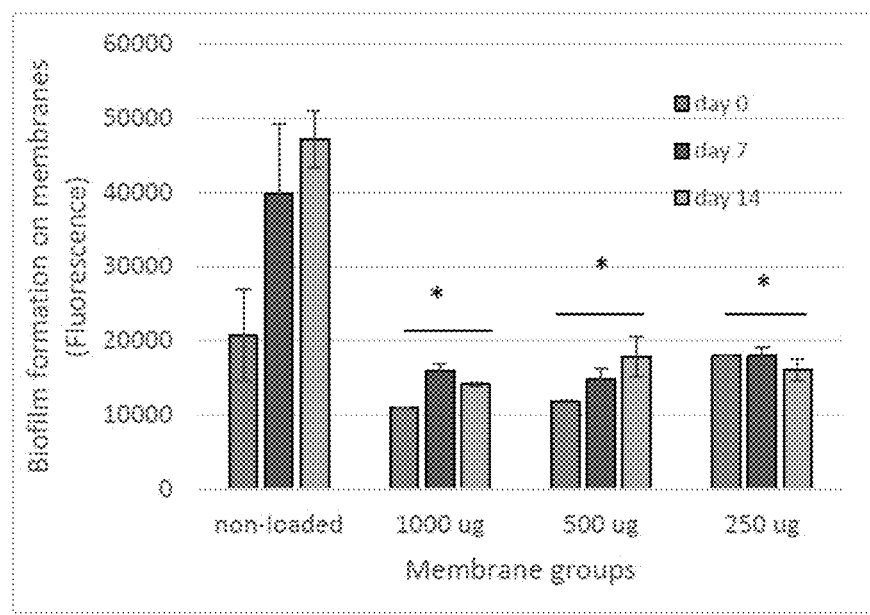
FIG. 5 shows the results of biofilm removed from chitosan membrane determined using PrestoBlue viability agent. Asterisks represent statistically significant differences from non-loaded membranes in two-way ANOVA with Holm Sidak post-tests.

While bacteria attached to the non-loaded membranes, 2-CP loaded membranes displayed significantly less bacterial attachment (FIG. 5). Bacterial attachment was significantly depressed even after 14 days of immersion in aqueous media, indicating that 2-CP loaded membranes inhibited biofilm formation.

Figure 6:
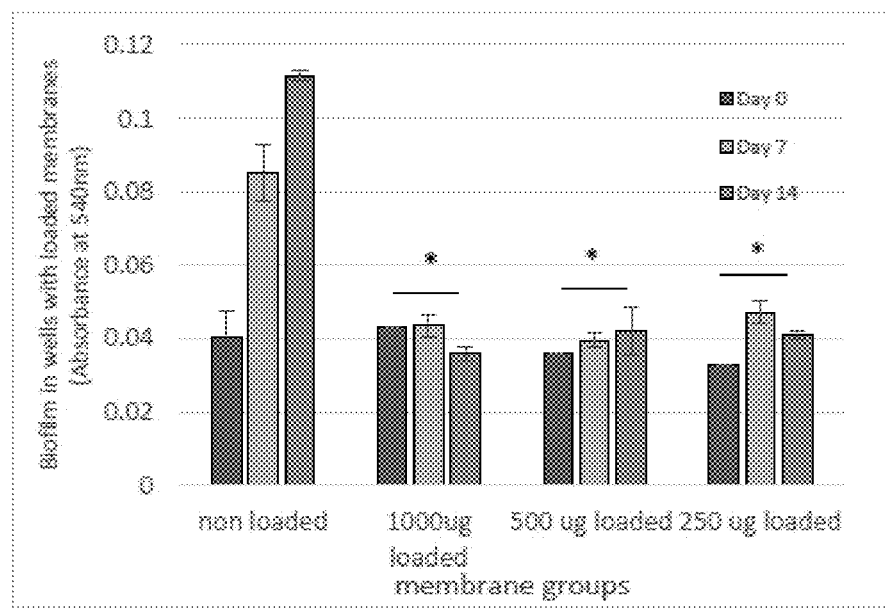
FIG. 6 shows the results of absorbance measurements (turbidity) of wells following removal of membranes loaded with the specified amount of 2-CP and washing in PBS. The absorbance measurements indicate the amount of biofilm deposition in the wells. Asterisks represent statistically significant differences from the non-loaded membranes in two-way ANOVA with Holm Sidak post-tests (p<0.05). Error bars are representative of standard deviation. N=5 for each group.

FIG. 6 compares the absorbances of each membrane to determine biofilm inhibition due to 2-CP release from the membranes. Biofilm formation in the wells adjacent to the membranes indicated that 2-CP loaded membranes inhibited biofilm formation in the wells (i.e., off the membrane as well). Accordingly, active 2-CP may be released from membranes for at least 14 days following loading.

Example 6: Biofilm Dispersion Measurements (*Pseudomonas aeruginosa*)

Biofilm was formed using *Pseudomonas aeruginosa* (ATCC 27317) in a 96-well plate format. Each well of the plate was seeded with 150 µL of bacterial culture and incubated for 24 hours. At 24 hours, each well received 135 µL of Tryptic soy broth (TSB) and 15 µL of C2DA, T2DA, or 2-CP were added to yield final concentrations of each test compound of 0, 125, or 250 µg/mL. The plate was then incubated for 24 hours and the medium was aspirated and the plate washed several times.

Figure 7:
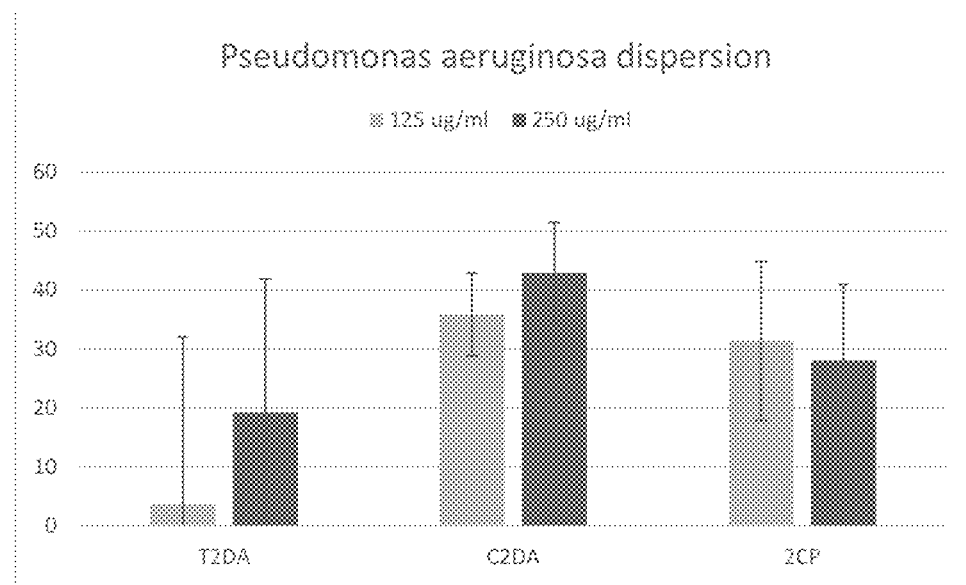
FIG. 7 illustrates the relative percentage of attached cells as compared to non-treated controls after exposure to T2DA, C2DA, or 2-CP as measured using a Luciferase assay for ATP production.

The relative percentage of attached cells as compared to non-treated controls was assessed using a Luciferase assay for ATP production. As can be seen in FIG. 7, 2-CP has increased ability to disperse biofilm as compared to T2DA and controls.

Example 7: Biofilm Inhibition

Synergy assays were performed to determine the effects of 2-CP when used in combination with various antimicrobials against gram positive *S. aureus* and gram negative *P. aeruginosa*. Amikacin, tetracycline, and levofloxacin were chosen for evaluation based on prior work demonstrating their synergistic effects with cis-2-decenoic acid. A checkerboard assay was prepared in 96-well plates with increasing anti-

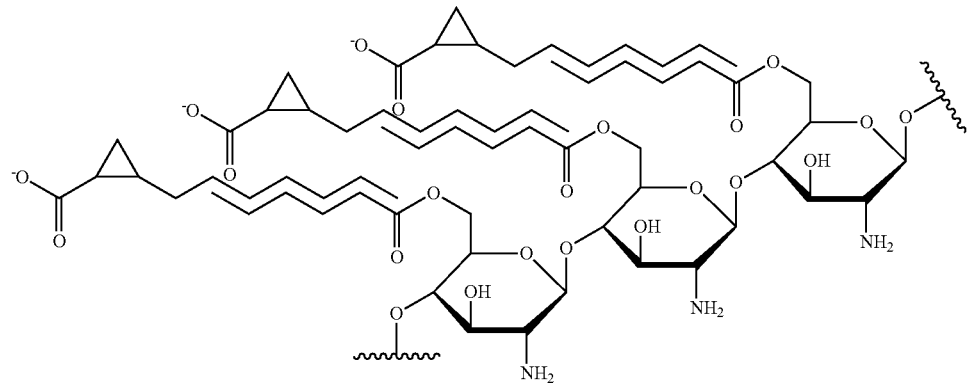

biotic concentration on the horizontal axis and increasing 2-CP concentration on the vertical axis. Final concentrations of 2-CP were 1000, 500, 250, 125, 62.5, 31.3, and 0 µg/mL. Final antibiotic concentrations varied based on their respective minimum inhibitory concentration for each organism and are given in Table 1. Each plate was then inoculated with *S. aureus* (UAMS-1) or *P. aeruginosa* (PA-ATCC 27317) overnight growths for a final dilution of 1 in 50 or 1 in 200, respectively, and incubated overnight. Inhibition was defined as a lack of visible growth after a 24 hr incubation period.

TABLE 1

Antibiotic concentrations tested in synergy assays

| Antibiotic | S. aureus | P. aeruginosa |
|---|---|---|
| Amikacin | 32, 16, 8 µg/mL | 4, 2, 1 µg/mL |
| Tetracycline | 1, 0.5, 0.25 µg/mL | 32, 16, 8 µg/mL |
| Levofloxacin | 1, 0.5, 0.25 µg/mL | 1, 0.5, 0.25 µg/mL |

The fractional inhibitory concentration index (FICI) was used to determine synergistic, additive, or antagonistic responses between the three antibiotics and 2-CP. To calculate the FICI, the MIC of the antibiotic in combination was divided by the MIC of the antibiotic alone, and added to the MIC of 2-CP in combination and divided by the MIC of 2-CP alone. FICI values less than or equal to 0.5 indicate synergy, values between 0.5-1 indicate additivity, values between 1-2 indicate indifference, and values above 2 indicate antagonism.

The fatty acid 2-CP was antimicrobial at high concentrations, inhibiting both *S. aureus* and *P. aeruginosa* growth at 4 mg/mL. Various concentrations of 2-CP were shown to effectively reduce the MIC of tobramycin, tetracycline, and levofloxacin against both strains by at least 50%. Tobramycin, tetracycline, and levofloxacin were found to have synergistic effects with 2-CP against *S. aureus* growth (Table 2). Only tobramycin was synergistic with 2-CP against *P. aeruginosa*, while tetracycline and levofloxacin were additive (Table 3).

TABLE 2

S. aureus fractional biofilm inhibitory concentration index values

| | S. aureus | | | | | |
|---|---|---|---|---|---|---|
| | MIC for 2-CP (alone) µg/mL | MIC for 2-CP (combined) µg/mL | MIC for antibiotic (alone) (µg/mL) | MIC for antibiotic (combined) (µg/mL) | FICI | Interpretation |
| Tobramycin | 4000 | 31 | 4 | 2 | 0.5 | synergistic |
| Tetracycline | 4000 | 62.5 | 1 | 0.5 | 0.5 | synergistic |
| Levofloxacin | 4000 | 500 | 1 | 0.25 | 0.4 | synergistic |

TABLE 3

P. aeruginosa fractional biofilm inhibitory concentration index values

| | P. aeruginosa | | | | | |
|---|---|---|---|---|---|---|
| | MIC for 2-CP (alone) µg/mL | MIC for 2-CP (combined) µg/mL | MIC for antibiotic (alone) µg/mL | MIC for antibiotic (combined) µg/mL | FICI | Interpretation |
| Tobramycin | 4000 | 31 | 0.5 | 0.25 | 0.5 | Synergistic |
| Tetracycline | 4000 | 1000 | 32 | 16 | 0.8 | Additive |
| Levofloxacin | 4000 | 1000 | 1 | 0.5 | 0.8 | Additive |

Example 8: Biofilm Eradication with Antibiotics

*Staphylococcus aureus* (UAMS1) was grown overnight in TSB by incubation at 37° C. *Pseudomonas aeruginosa* (ATCC 27317) was grown overnight in a similar manner. *S. aureus* was diluted 1:10 in TSB and *P. aeruginosa* was diluted 1:50. Bacterial dilutions were added at a volume of 150 µL into each well of a 96-well MBEC' Biofilm Inoculator plate, followed by overnight incubation to form the biofilm. The next day the medium from each well was carefully aspirated allowing the biofilm to remain both on the pegs of the top plate and the bottom of the wells. Stocks of tobramycin and tetracycline as well as varying concentrations of 2-CP were added to the wells. These plates were incubated at 37° C. for 24 hours. The next day the peg plates (top plate) were removed and added to new plates containing 150 µL of sterile TSB in each well. Plates were sonicated for 5 minutes to remove the viable bacteria attached to the peg surface and later incubated for 24 hours. Turbidity was measured by reading absorbance at 540 nm for bacterial growth in the presence of fixed concentrations of the antibiotics with varying concentrations of 2-CP and C2DA.

The fatty acid 2-CP did not eradicate biofilm at any concentration tested and 4000 µg/mL was used for calculating FICI. 2-CP had additive effects in eradication of both *S. aureus* and *P. aeruginosa* in combination with tobramycin (Table 4). Synergistic eradication effects of *P. aeruginosa* were found when 2-CP was combined with levofloxacin (Table 4). Tetracycline did not eradicate *P. aeruginosa* at any concentration evaluated, so FICI was not determined. Tetracycline did demonstrate additive effects in eradication of *S. aureus* (Table 4)

TABLE 4

Fractional Biofilm Eradication Index values
P. aeruginosa

| | MEC for 2-CP (alone) | MEC for 2-CP (combined) | MEC for antibiotic (alone) (µg/mL) | MEC for antibiotic (combined) (µg/mL) | FICI | Interpretation |
|---|---|---|---|---|---|---|
| Tobramycin | >4000 | 250 | 0.5 | 0.25 | 0.5625 | Additive |
| Tetracycline | >4000 | ND | ND | ND | ND | ND |
| Levofloxacin | >4000 | 250 | 0.3 | 0.08 | 0.33 | Synergistic |

TABLE 4-continued

| | | | S. aureus | | | |
|---|---|---|---|---|---|---|
| | MEC for 2-CP (alone) | MEC for 2-CP (combined) | MEC for antibiotic (alone) (µg/mL) | MEC for antibiotic (combined) (µg/mL) | FICI | Interpretation |
| Tobramycin | >4000 | 31.25 | 2.5 | 1.25 | 0.51 | Additive |
| Tetracycline | >4000 | 125 | 1.25 | 0.625 | 0.53 | Additive |

As various changes can be made in the above-described subject matter without departing from the scope and spirit of the present invention, it is intended that all subject matter contained in the above description, or defined in the appended claims, be interpreted as descriptive and illustrative of the present invention. Many modifications and variations of the present invention are possible in light of the above teachings. Accordingly, the present description is intended to embrace all such alternatives, modifications and variances which fall within the scope of the appended claims.

The invention claimed is:

1. A method of inhibiting biofilm formation on a surface comprising inserting one or more compounds derived from a mono-unsaturated fatty acid onto said surface, wherein said compound is cyclopropanated at the double bond of said fatty acid, and wherein said compound is effective to inhibit biofilm formation, wherein said compound has the structure according to formula (I):

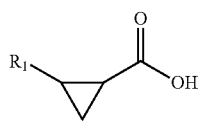

(I)

wherein $R_1$ is a $C_5$-$C_{24}$ linear or branched alkyl group.

2. The method according to claim 1, wherein said surface comprises chitosan and/or chitin.

3. The method according to claim 1, wherein said compound is adsorbed on said surface.

4. The method according to claim 1, wherein said compound is covalently attached to said surface.

5. The method according to claim 1, wherein said compound has the structure according to formula (Ia) or (Ib):

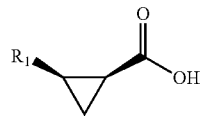

(Ia)

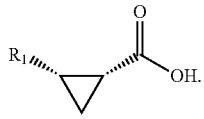

(Ib)

6. The method according to claim 1, wherein said compound selected from one of the following structures:

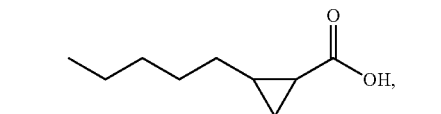

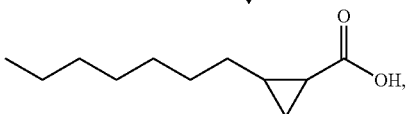

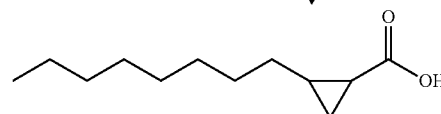

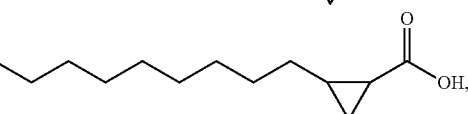

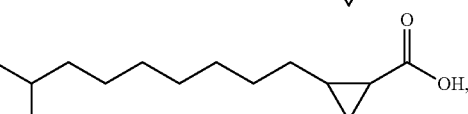

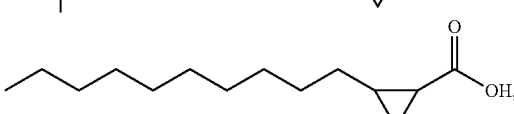

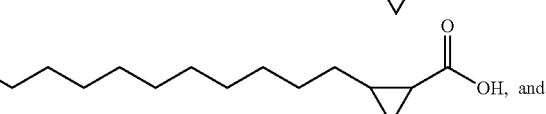, and

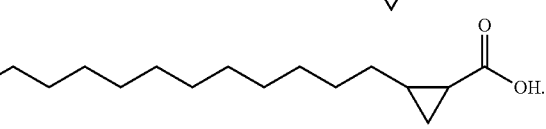

7. The method according to claim 1, wherein said biofilm is produced by an organism selected from bacteria, algae, fungi, and protozoa.

* * * * *